(12) United States Patent
Field et al.

(10) Patent No.: US 11,452,470 B2
(45) Date of Patent: Sep. 27, 2022

(54) DEVICES, SYSTEMS, AND METHODS USING WEARABLE TIME DOMAIN-BASED ACTIVITY TRACKER

(71) Applicant: HI LLC, Los Angeles, CA (US)

(72) Inventors: Ryan Field, Culver City, CA (US); Michael Henninger, Austin, TX (US); Katherine Perdue, Los Angeles, CA (US); Isai Olvera, South Portland, ME (US); Hamid Dehghani, Birmingham (GB); Julian Kates-Harbeck, Marina Del Rey, CA (US); Antonio H. Lara, Valencia, CA (US); Bryan Johnson, Culver City, CA (US); Victoria A. Poissant, Northridge, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 17/550,387

(22) Filed: Dec. 14, 2021

(65) Prior Publication Data
US 2022/0211300 A1    Jul. 7, 2022

Related U.S. Application Data

(60) Provisional application No. 63/179,080, filed on Apr. 23, 2021, provisional application No. 63/160,995, (Continued)

(51) Int. Cl.
*A61B 5/1455* (2006.01)
*A61B 5/00* (2006.01)
*A61B 5/0205* (2006.01)

(52) U.S. Cl.
CPC ........ *A61B 5/14551* (2013.01); *A61B 5/0205* (2013.01); *A61B 5/14552* (2013.01); (Continued)

(58) Field of Classification Search
CPC .............. A61B 5/1455; A61B 5/14551; A61B 5/14552; A61B 5/681; A61B 5/742; (Continued)

(56) References Cited

U.S. PATENT DOCUMENTS 5,386,827 A    2/1995   Chance et al.
5,431,170 A *  7/1995   Mathews ............... A61B 5/681
                                                         600/323

(Continued)

FOREIGN PATENT DOCUMENTS

WO    2018033751    2/2018

OTHER PUBLICATIONS

Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680.

(Continued)

*Primary Examiner* — Eric F Winakur
(74) *Attorney, Agent, or Firm* — ALG Intellectual Property, LLC

(57) ABSTRACT

An illustrative optical measurement device includes a light source configured to emit light pulses directed at a target. The optical measurement device further includes a detector configured to detect arrival times for photons of the light pulses after the photons are scattered by the target. The optical measurement device further includes a processing unit configured to generate, based on the arrival times of the photons at the detector, histogram data associated with the target. The processing unit is further configured to determine, based on the histogram data, an absolute optical property associated with the target. The processing unit is further configured to determine, based on the absolute (Continued)

optical property, a blood oxygenation level of the user, and perform an operation based on the blood oxygenation level.

24 Claims, 16 Drawing Sheets

Related U.S. Application Data filed on Mar. 15, 2021, provisional application No. 63/154,116, filed on Feb. 26, 2021, provisional application No. 63/134,479, filed on Jan. 6, 2021.

(52) U.S. Cl.
CPC ............ *A61B 5/681* (2013.01); *A61B 5/6826* (2013.01); *A61B 5/7271* (2013.01); *A61B 5/742* (2013.01); *A61B 5/746* (2013.01); *A61B 2562/0238* (2013.01)

(58) Field of Classification Search
CPC ... A61B 5/7271; A61B 5/746; A61B 5/02416; A61B 5/08; A61B 5/4812
See application file for complete search history.

(56) References Cited

U.S. PATENT DOCUMENTS

| | | | |
|---|---|---|---|
| 5,490,523 A * | 2/1996 | Isaacson | A61B 5/6826 600/323 |
| 5,853,370 A | 12/1998 | Chance et al. | |
| 6,240,309 B1 | 5/2001 | Yamashita et al. | |
| 6,384,663 B2 | 5/2002 | Cova et al. | |
| 6,640,133 B2 | 10/2003 | Yamashita | |
| 6,683,294 B1 | 1/2004 | Herbert et al. | |
| 6,839,583 B1 * | 1/2005 | Lewandowski | A61B 5/14552 600/344 |
| 7,356,365 B2 | 4/2008 | Schurman | |
| 7,547,872 B2 | 6/2009 | Niclass et al. | |
| 7,774,047 B2 | 8/2010 | Yamashita et al. | |
| 8,026,471 B2 | 9/2011 | Itzler | |
| 8,078,250 B2 | 12/2011 | Chen et al. | |
| 8,082,015 B2 | 12/2011 | Yodh et al. | |
| 8,633,431 B2 | 1/2014 | Kim | |
| 8,817,257 B2 | 8/2014 | Herve | |
| 9,058,081 B2 | 6/2015 | Baxter | |
| 9,076,707 B2 | 7/2015 | Harmon | |
| 9,131,861 B2 | 9/2015 | Ince et al. | |
| 9,316,735 B2 | 4/2016 | Baxter | |
| 9,401,448 B2 | 7/2016 | Bienfang et al. | |
| 9,419,635 B2 | 8/2016 | Kumar et al. | |
| 9,442,201 B2 | 9/2016 | Schmand et al. | |
| 9,529,079 B1 | 12/2016 | Droz | |
| 9,574,936 B2 | 2/2017 | Heinonen | |
| 9,579,060 B1 | 2/2017 | Lisy et al. | |
| 9,946,344 B2 | 4/2018 | Ayaz et al. | |
| D817,553 S | 5/2018 | Aaskov et al. | |
| D825,112 S | 8/2018 | Saez | |
| 10,158,038 B1 | 12/2018 | Do Valle et al. | |
| 10,340,408 B1 | 7/2019 | Katnani | |
| 10,424,683 B1 | 9/2019 | Do Valle | |
| 10,515,993 B2 | 12/2019 | Field et al. | |
| 10,697,829 B2 | 6/2020 | Delic | |
| 10,772,561 B2 | 9/2020 | Donaldson | |
| 10,809,796 B2 | 10/2020 | Armstrong-Muntner | |
| 10,912,504 B2 | 2/2021 | Nakaji | |
| 11,006,876 B2 | 5/2021 | Johnson | |
| 11,006,878 B2 | 5/2021 | Johnson | |
| 2007/0083097 A1 | 4/2007 | Fujiwara | |
| 2009/0012402 A1 | 1/2009 | Mintz | |
| 2011/0208675 A1 | 8/2011 | Shoureshi et al. | |
| 2012/0184831 A1 | 7/2012 | Seetamraju et al. | |
| 2013/0342835 A1 | 12/2013 | Blacksberg | |
| 2014/0088378 A1 | 3/2014 | Muzet | |
| 2014/0191115 A1 | 7/2014 | Webster et al. | |
| 2014/0217264 A1 | 8/2014 | Shepard | |
| 2014/0275891 A1 | 9/2014 | Muehlemann et al. | |
| 2015/0038811 A1 | 2/2015 | Asaka | |
| 2015/0041625 A1 | 2/2015 | Dutton | |
| 2015/0054111 A1 | 2/2015 | Niclass et al. | |
| 2015/0077279 A1 | 3/2015 | Song | |
| 2015/0150505 A1 | 6/2015 | Kaskoun et al. | |
| 2015/0327777 A1 | 11/2015 | Kostic et al. | |
| 2015/0364635 A1 | 12/2015 | Bodlovic et al. | |
| 2017/0030769 A1 | 2/2017 | Clemens et al. | |
| 2017/0052065 A1 | 2/2017 | Sharma et al. | |
| 2017/0176596 A1 | 6/2017 | Shpunt et al. | |
| 2017/0179173 A1 | 6/2017 | Mandai et al. | |
| 2017/0202518 A1 | 7/2017 | Furman et al. | |
| 2017/0281086 A1 | 10/2017 | Donaldson | |
| 2017/0363467 A1 | 12/2017 | Clemens et al. | |
| 2017/0367650 A1 | 12/2017 | Wallois | |
| 2018/0014741 A1 | 1/2018 | Chou | |
| 2018/0027196 A1 | 1/2018 | Yang et al. | |
| 2018/0039053 A1 | 2/2018 | Kremer et al. | |
| 2018/0070830 A1 * | 3/2018 | Sutin | A61B 5/14553 |
| 2018/0070831 A1 | 3/2018 | Sutin et al. | |
| 2018/0089848 A1 | 3/2018 | Yang et al. | |
| 2018/0192931 A1 | 7/2018 | Linden et al. | |
| 2019/0113385 A1 | 4/2019 | Fukuchi | |
| 2019/0175068 A1 | 6/2019 | Everdell | |
| 2019/0355861 A1 | 11/2019 | Katnani | |
| 2019/0363210 A1 | 11/2019 | Do Valle | |
| 2019/0388018 A1 | 12/2019 | Horstmeyer | |
| 2020/0060542 A1 | 2/2020 | Alford | |
| 2020/0116838 A1 | 4/2020 | Erdogan | |
| 2020/0196932 A1 | 6/2020 | Johnson | |
| 2020/0253479 A1 | 8/2020 | Nurmikko | |
| 2020/0315510 A1 | 10/2020 | Johnson | |
| 2020/0337624 A1 | 10/2020 | Johnson | |
| 2020/0390358 A1 | 12/2020 | Johnson | |

OTHER PUBLICATIONS

Ban, et al., "Kernel Flow: a high channel count scalable TD-fNIRS system", https://www.spiedigitallibrary.org/conference-proceedings-of-spie Proc. of SPIE vol. 11663, 116630B CCC code: 1605-7422/21/$21 doi: 10.1117/12.2582888.

Contini, et al., "Photon migration through a turbid slab described by a model based on diffusion approximation. I. Theory", Appl. Opt. 36(19), 4587 (1997).

Di Sieno, et al., "Probe-hosted large area silicon photomultiplier and high-throughput timing electronics for enhanced performance time-domain functional near-infrared spectroscopy", Biomed Opt. Express 11(11), 6389 (2020).

Feiner, et al., Dark Skin Decreases the Accuracy of Pulse Oximeters at Low Oxygen Saturation: The Effects of Oximeter Probe Type and Gender, Anesthesia & Analgesia; vol. 105, No. 5, Dec. 2007.

Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.

Hua, et al., "A pulse oximeter based on Time-of-Flight histograms", Proceedings vol. 11693, Photonic Instrumentation Engineering VIII; 116930G (2021) https://doi.org/10.1117/12.2577757.

Huppert, et al., "HomER: a review of time-series analysis methods for near-infrared spectroscopy of the brain", Appl. Opt. 48(10), D280 (2009).

Kavsaoglu, et al., "Non-invasive prediction of hemoglobin level using machine learning techniques with the PPG signal's characteristics features", Applied Soft Computing 37 (2015) 983-991. http://dx.doi.org/10.1016/j.asoc.2015.04.008. 1568-4946/© 2015 Elsevier.

Kienle, et al., "Improved solutions of the steady-state and the time-resolved diffusion equations for reflectance from a semi-infinite turbid medium", J. Opt. Soc. Am. A 14(1), 246 (1997).

Kim, et al., "Stress and Heart Rate Variability: A Meta-Analysis and Review of the Literature", Psychiatry Investig 2018;15(3):235-245, https://doi.org/10.30773/pi.2017.08.17 Print ISSN 1738-3684 / Online ISSN 1976-3026.

(56) References Cited

OTHER PUBLICATIONS

Konugolu, et al., "Broadband (600-1350 nm) Time-Resolved Diffuse Optical Spectrometer for Clinical Use", IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring", Biomed. Opt. Express 11(10), 5934 (2020).

Lange, et al., "Clinical Brain Monitoring with Time Domain NIRS: A Review and Future Perspectives", Applied Sciences 9(8), 1612 (2019).

Lange, et al., "MAESTROS: A Multiwavelength Time-Domain NIRS System to Monitor Changes in Oxygenation and Oxidation State of Cytochrome-C-Oxidase", IEEE J. Select. Topics Quantum Electron. 25(1), 1-12 (2019).

Leonard, et al., "Changes in Heart Rate Variability During Heartfulness Meditation: A Power Spectral Analysis Including the Residual Spectrum", Front. Cardiovasc. Med. 6:62 doi: 10.3389/fcvm.2019.00062.

Mannheimer, et al., "The Light-Tissue Interaction of Pulse Oximetry", Anesthesia & Analgesia; Dec. 2007; vol. 105, No. 6: S10-7. doi:10.1213/01.ane.0000269522.84942.54. PMID: 18048891.

Martelli, et al., "Optimal estimation reconstruction of the optical properties of a two-layered tissue phantom from time-resolved single-distance measurements", Journal of Biomedical Optics 20(11), 115001 (Nov. 2015).

Mora, et al., "Fast silicon photomultiplier improves signal harvesting and reduces complexity in time-domain diffuse optics". Opt. Express 23(11), 13937 (2015).

Pifferi, et al., "Performance assessment of photon migration instruments: the MEDPHOT protocol", Applied Optics, 44(11), 2104-2114.

Prahl, et al., "Optical Absorption of Hemoglobin", http://omlc.ogi.edu/spectra/hemoglobin/index.html.

Re, et al., "Multi-channel medical device for time domain functional near infrared spectroscopy based on wavelength space multiplexing", Biomed. Opt. Express 4(10), 2231 (2013).

Renna, et al., "Eight-Wavelength, Dual Detection Channel Instrument for Near-Infrared Time-Resolved Diffuse Optical Spectroscopy", IEEE J. Select. Topics Quantum Electron. 25(1), 1-11 (2019).

Torricelli, et al., "Time domain functional NIRS imaging for human brain mapping", NeuroImage 85, 28-50 (2014).

Wabnitz, et al., "Depth-selective data analysis for time-domain fNIRS: moments vs. time windows", Biomed. Opt. Express 11(8), 4224 (2020).

Wabnitz, et al., "Performance assessment of time-domain optical brain imagers, part 1: basic instrumental performance protocol", Journal of Biomedical Optics 19(8), 086010 (Aug. 2014).

Wabnitz, et al., "Performance assessment of time-domain optical brain imagers, part 2: nEUROPt protocol", Journal of Biomedical Optics 19(8), 086012 (Aug. 2014).

Wojtkiewicz, et al., "Self-calibrating time-resolved near infrared spectroscopy", Biomed. Opt. Express 10(5), 2657 (2019).

Zucchelli, et al., "Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893.

Laput, et al., "Skin Buttons: Cheap, Small, Low-Power and Clickable Fixed-Icon Laser Projections", User Interface Software and Technology, ACM, Oct. 5, 2014, pp. 389-394.

"International Search Report and Written Opinion dated Apr. 13, 2022 in corresponding International Application No. PCT/US2021/063375, with an international filing date date of Dec. 14, 2021".

\* cited by examiner

DEVICES, SYSTEMS, AND METHODS USING WEARABLE TIME DOMAIN-BASED ACTIVITY TRACKER

RELATED APPLICATIONS

The present application claims priority under 35 U.S.C. § 119(e) to U.S. Provisional Patent Application No. 63/134,479, filed on Jan. 6, 2021; U.S. Provisional Patent Application No. 63/154,116, filed on Feb. 26, 2021; U.S. Provisional Patent Application No. 63/160,995, filed on Mar. 15, 2021; and U.S. Provisional Patent Application No. 63/179,080, filed on Apr. 23, 2021. These applications are incorporated herein by reference in their respective entireties.

BACKGROUND INFORMATION

Optical-based pulse oximeters are widely used to measure heart rates and blood oxygenation levels. These optical devices are designed to record these types of measurements non-invasively and may provide continuous monitoring of the blood oxygenation levels, which may enable better observation of users than non-continuous means for measuring blood oxygenation. The devices may measure blood oxygenation levels such as peripheral oxygen saturation ($SpO_2$), which may be used to estimate arterial oxygen saturation ($SaO_2$).

Typically, conventional pulse oximeters rely on changes in absorption as measured with two or more wavelengths in the red and infrared range. These measurements allow for estimation of blood oxygenation levels due to the differences in absorption of oxygenated and deoxygenated hemoglobin at the particular wavelengths. However, these relative measurements may be susceptible to error due to various factors including physiological variables that may lead to inaccurate blood oxygenation level readings.

BRIEF DESCRIPTION OF THE DRAWINGS

The accompanying drawings illustrate various embodiments and are a part of the specification. The illustrated embodiments are merely examples and do not limit the scope of the disclosure, Throughout the drawings, identical or similar reference numbers designate identical or similar elements.

DETAILED DESCRIPTION

In accordance with the systems and methods described herein, an optical measurement device may include a light source configured to emit light pulses directed at a target. The optical measurement device may further include a detector configured to detect arrival times for photons of the light pulses after the photons are scattered by the target. The optical measurement device may further include a processing unit configured to generate, based on the arrival times of the photons at the detector, histogram data associated with the target. The processing unit may further be configured to determine, based on the histogram data, an absolute optical property associated with the target. The processing unit may further be configured to determine, based on the absolute optical property, a blood oxygenation level of the user. The processing unit may further be configured to perform an operation based on the blood oxygenation level.

For example, an optical measurement device may be configured to determine a blood oxygenation level of a user, similar to conventional pulse oximeters. However, unlike conventional pulse oximeters, the optical measurement device may use time-resolved techniques described herein to determine the absolute coefficients of absorption ($\mu a$) and reduced scattering ($\mu s'$) of tissue of a user. From these absolute optical properties, the tissue oxygenation may be determined through the Beer-Lambert Law. This approach for determining the oxygenation level may allow for an absolute measurement of the bulk tissue properties that leads to quantified oxygenation levels that is less susceptible to errors due to changes in skin color and calibration of the relative measurements used by conventional pulse oximeters.

Further, the histogram data generated by the time-resolved techniques may allow the optical measurement device to determine at a high resolution additional characteristics of the user, such as heart rate, respiratory rate, and/or heart rate variability. Such high-resolution measurements may allow for additional determinations of characteristics associated with the user (e.g., sleep stages, etc.) with a higher accuracy than conventional systems.

These and other advantages and benefits of the present systems and methods are described more fully herein.

Figure 1:
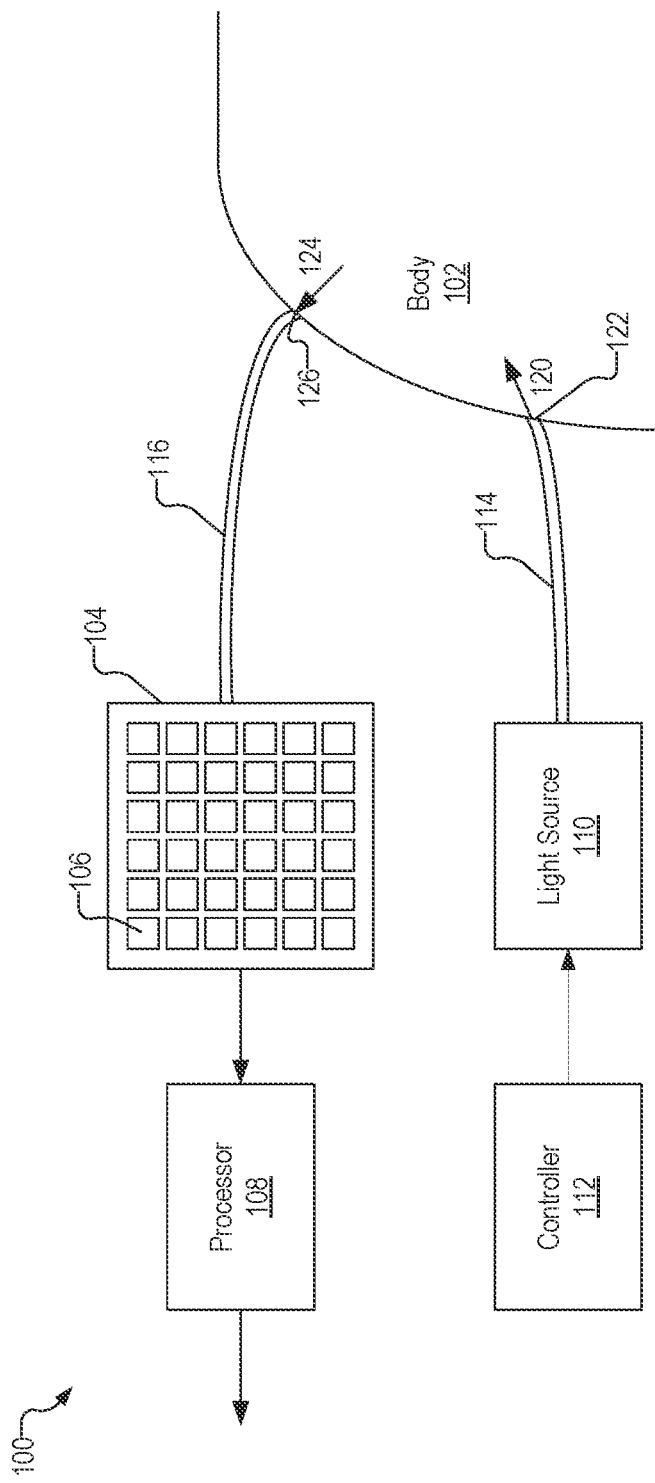
FIG. 1 illustrates an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021, published as US2021/0259638A1; U.S. patent application Ser. No. 17/176,309, filed Feb. 16, 2021, published as US 2021/0259614A1; U.S. patent application Ser. No. 17/176,460, filed Feb. 16, 2021, issued as U.S. Pat. No. 11,096,620; U.S. patent application Ser. No. 17/176,470, filed Feb. 16, 2021, published as US2021/0259619A1; U.S. patent application Ser. No. 17/176,487, filed Feb. 16, 2021, published as US2021/0259632A1; U.S. patent application Ser. No. 17/176,539, filed Feb. 16, 2021, published as US2021/0259620A1; U.S. patent application Ser. No. 17/176,560, filed Feb. 16, 2021, published as US2021/0259597A1; U.S. patent application Ser. No. 17/176,466, filed Feb. 16, 2021, published as US2021/0263320A1, and Han Y. Ban, et al., "Kernel Flow: A High Channel Count Scalable TD-fNIRS System," SPIE Photonics West Conference (Mar. 6, 2021), which applications and publications are incorporated herein by reference in their entirety.

In some examples, optical measurement operations performed by optical measurement system 100 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain digital optical tomography (TD-DOT).

Optical measurement system 100 (e.g., an optical measurement system that is implemented by a wearable device or other configuration, and that employs a time domain-based (e.g., TD-NIRS) measurement technique) may detect blood oxygenation levels and/or blood volume levels by measuring the change in shape of laser pulses after they have passed through target tissue, e.g., brain, muscle, finger, etc. As used herein, a shape of laser pulses refers to a temporal shape, as represented for example by a histogram generated by a time-to-digital converter (TDC) coupled to an output of a photodetector, as will be described more fully below.

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as 2$^n$ photodetectors (e.g., 256, 512 , . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diode (mLEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head, hand, wrist, finger, foot, chest, ear, or any other body part of a human or other animal. Alternatively, body 102 may be a non-living object. For illustrative purposes, it will be assumed in the examples provided herein that body 102 is a human head, human hand, human wrist, human finger, human earlobe, human foot, or human toe.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject, to the skin of the subject's hand or finger, or to any other location on body 102). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102, In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

Figure 2:
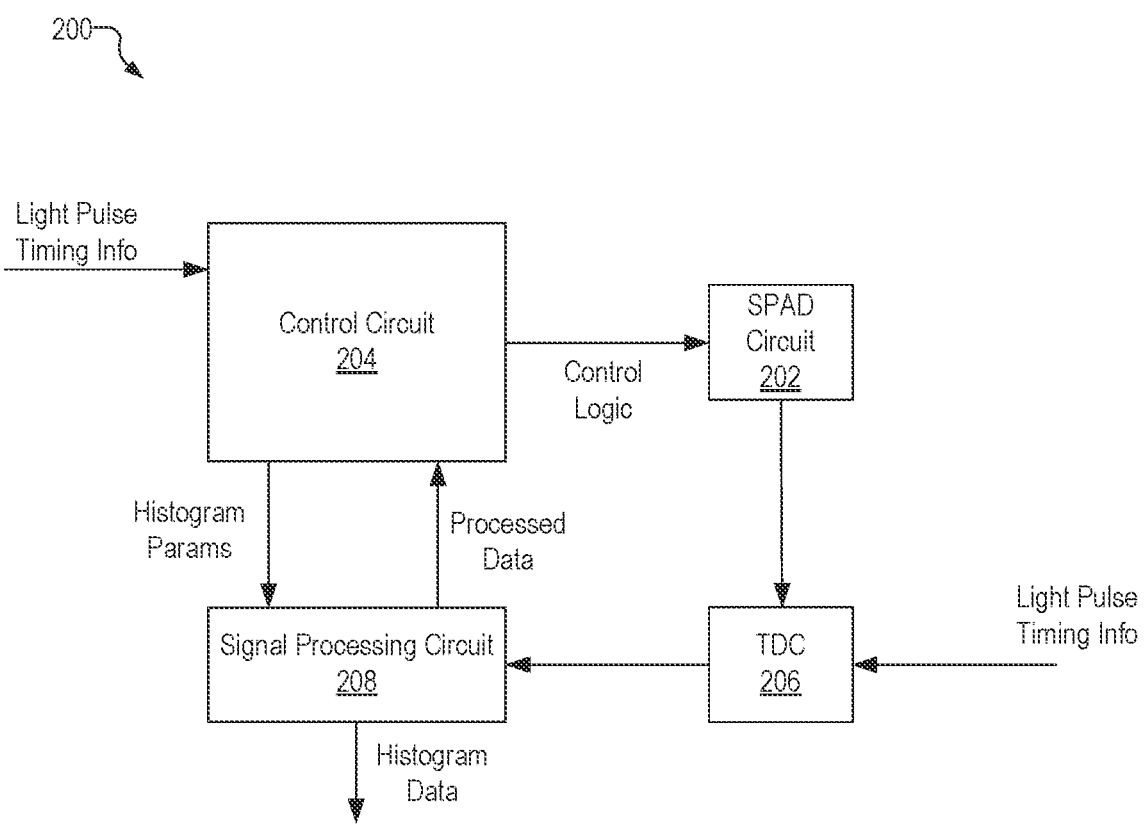
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters.

In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
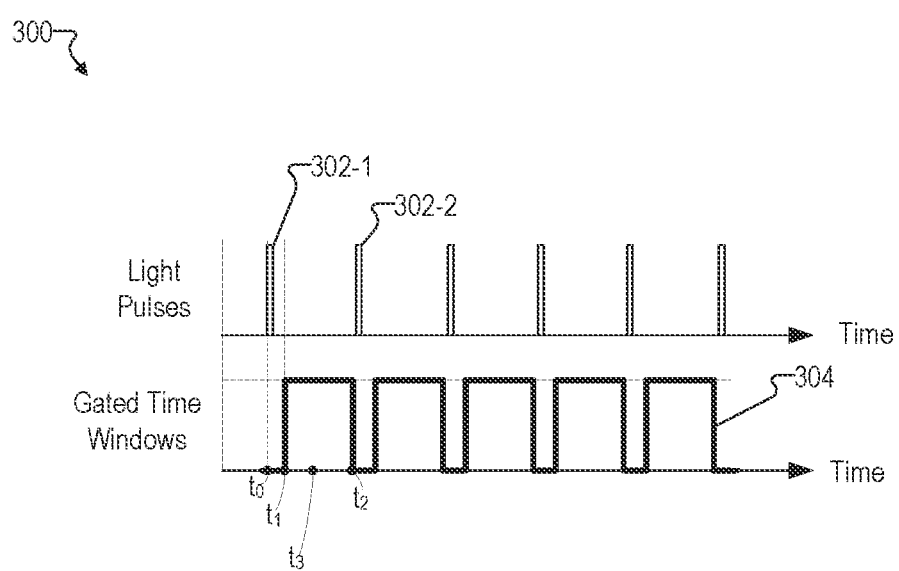
FIG. 3 illustrates an exemplary timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a finger of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time $t_0$. At a time $t_1$, a first instance of the predetermined gated time window begins. Photodetectors 106 may be armed at time $t_i$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
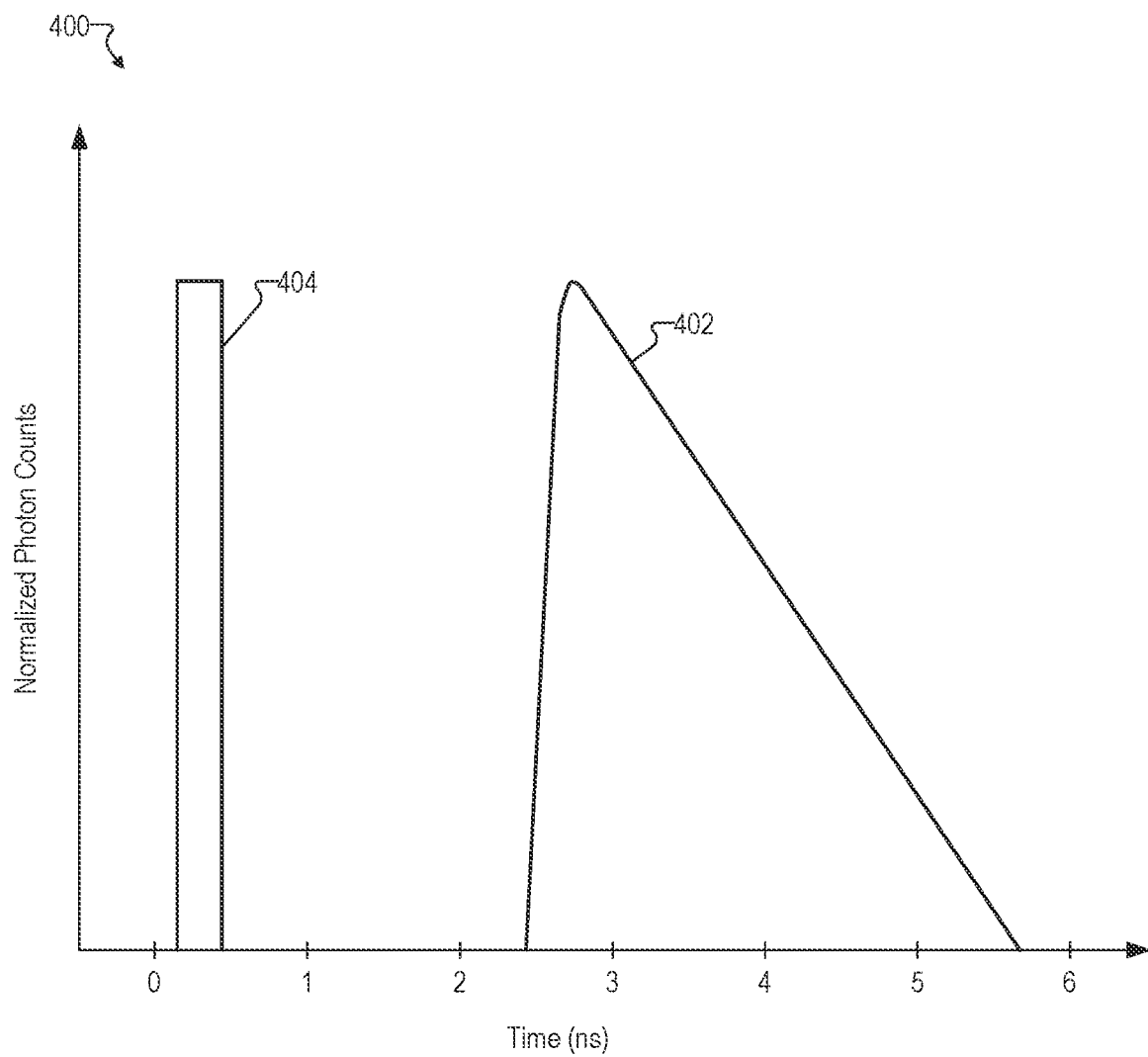
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological activity.

Figure 5:
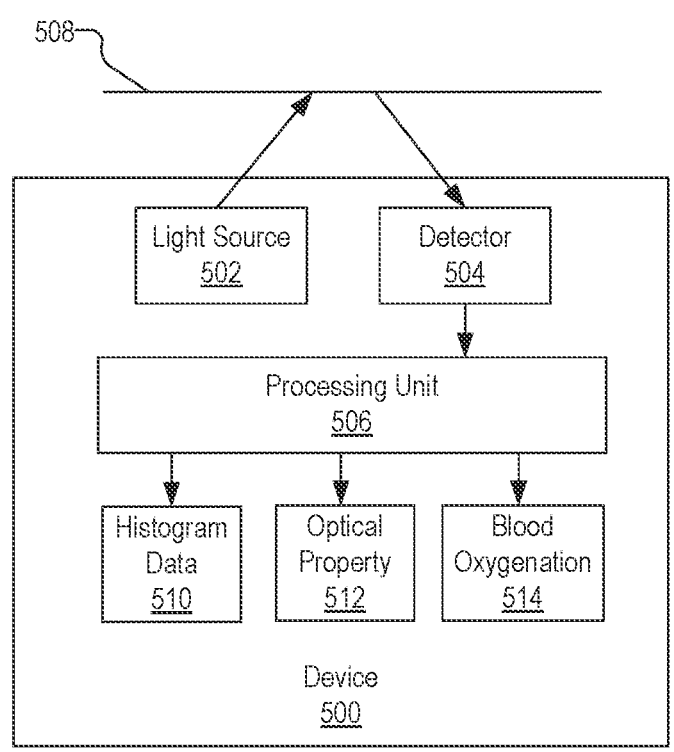
FIG. 5 illustrates an exemplary optical measurement device in accordance with the systems and methods described herein.

FIG. 5 illustrates an exemplary optical measurement device 500 ("device") that may include an implementation of optical measurement system 100 and/or a portion of optical measurement system 100. Device 500 includes a light source 502 (e.g., an implementation of light source 110), a detector 504 (e.g., an implementation of detector 104) and a processing unit 506. Processing unit 506 may be implemented by processor 108, controller 112, control circuit 204, and/or any other suitable processing and/or computing device or circuit. An exemplary implementation of processing unit 506 is described herein.

Light source 502 may be configured to direct light (e.g., light pulses) at a target 508 (e.g., body 102). Detector 504 may be configured to detect photons of the light emitted by light source 502 after the light is scattered by target 508. Detector 504 may detect arrival times of the photons at detector 504 and provide output data to processing unit 506 indicating the arrival times. Processing unit 506 may generate, based on the arrival times, histogram data 510 associated with target 508.

Processing unit 506 may determine, based on histogram data 510, an optical property 512 associated with target 508. Optical property 512 may include an absolute optical property, which may be contrasted from a relative optical property. For instance, absolute optical properties may include an absorption coefficient ($\mu a$), a reduced scattering coefficient ($\mu s'$), or any other such absolute measurements of optical properties. In contrast, relative optical properties may include measuring changes in an absorption or other optical property. When such relative optical property measurements are used to determine a blood oxygenation level (e.g., a peripheral oxygen saturation, an arterial oxygen saturation, etc.), the determined blood oxygenation level may be inaccurate due to various physiological factors (e.g., skin color), Thus, it may be advantageous to measure absolute optical properties associated with target 508 and determine blood oxygenation level and other characteristics associated with the user, as enabled by systems and methods described herein.

Based on optical property 512, processing unit 506 may determine a blood oxygenation level 514 of a user (e.g., a wearer of device 500). For instance, processing unit 506 may use the Beer-Lambert Law to determine a peripheral oxygen saturation based on $\mu a$ and/or $\mu s'$. Based on the peripheral oxygen saturation, processing unit 506 may further determine an arterial oxygen saturation level of the user.

Processing unit 506 may further perform an operation based on the blood oxygenation level. For instance, processing unit 506 may provide the blood oxygenation level for display, provide an output (e.g., an alert, a display of information, etc.) based on the blood oxygenation level meeting a threshold blood oxygenation level, present content (e.g., a recommendation, a graph or a graphic or other depiction, etc.) associated with the blood oxygenation level, use the blood oxygenation level for further determining other characteristics associated with the user, etc.

Additionally or alternatively, processing unit 506 may determine one or more other characteristics associated with the user based on histogram data 510. Histogram data 510 may be captured at a high sampling rate (e.g., 1 kilohertz (kHz)), which may generate histogram data 510 with a sufficiently high resolution to determine a variety of characteristics associated with the user. For example, processing unit 506 may determine a respiratory rate of the user, a heart rate of the user, a heart rate variability of the user, or any other suitable characteristic that may be determined based on histogram data 510.

Additionally or alternatively, processing unit 506 may access additional information associated with the user and combine such information with determined characteristics to further determine additional characteristics associated with the user. For instance, processing unit 506 may access inertial measurement unit (IMU) data associated with the user. Such IMU data may be determined by other components (e.g., an IMU, an accelerometer, a gyroscope, a magnetometer, etc.) of device 500 and/or other devices and provided to processing unit 506. Processing unit 506 may determine a sleep stage of the user based on the IMU data and one or more characteristics (e.g., the respiratory rate, heart rate, and/or heart rate variability of the user), wherein such characteristics are determined based on histogram data 510.

Figure 6:
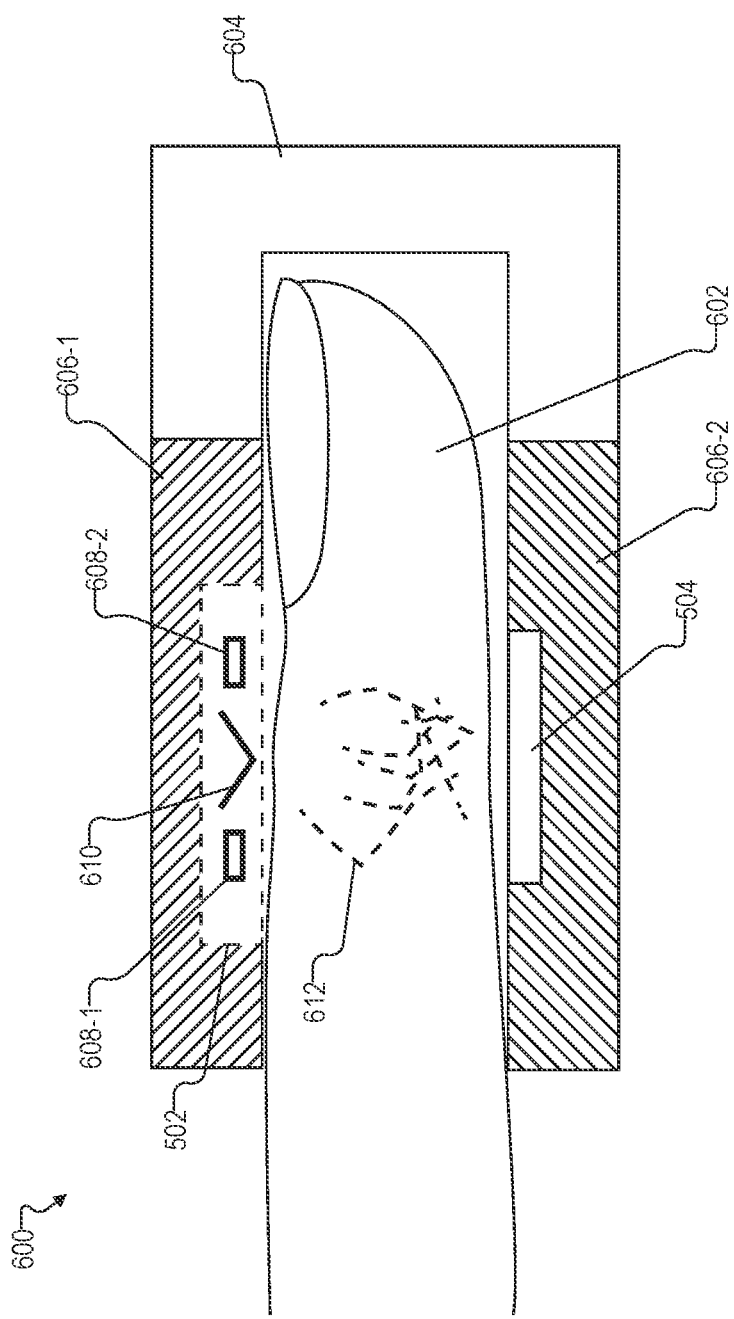
FIGS. 6-10 show a variety of geometries and form factors of optical measurement devices that may be used in accordance with the systems and methods described herein.

FIG. 6 illustrates an exemplary configuration 600 of optical measurement device 500 that may be worn on a finger 602 of a user. While a finger 602 is illustrated in FIG. 6, it will be recognized that configuration 600 (and/or any of the other configurations described herein) may alternatively be worn on any other appendage of the user.

As shown, configuration 600 includes a housing 604 that is configured to fit on finger 602. Housing 604 includes a first portion 606-1 configured to contact a first side of finger 602 and a second portion 606-2 configured to contact a second side of finger 602 while finger 602 is inserted into housing 604. In configuration 600, portion 606-1 is configured to house light source 502 and portion 606-2 configured to house detector 504. While not shown in FIG. 6, configuration 600 may further include processing unit 506, which may be housed in housing 604 at any suitable location.

In configuration 600, light source 502 may be implemented by two lasers 608 (e.g., laser 608-1 and laser 608-2) and a prism 610. Lasers 608 may be implemented by vertical-cavity surface-emitting lasers (VCSELs) or any other suitable laser or light source and may be configured to direct light pulses at prism 610, which may be configured to redirect the light pulses toward finger 602. As represented by dashed lines 612, the light pulses are scattered by and pass through finger 602 from light source 502 to detector 504.

In this example, as light source 502 is housed in portion 606-1 of housing 604 and detector 504 is housed in portion 606-2 of housing 604, light source 502 may be positioned on an opposite side of finger 602 from detector 504. While configuration 600 shows portion 606-1 positioning light source 502 on top of finger 602 and portion 606-2 positioning detector 504 on a bottom of finger 602, housing 604 may be alternatively oriented such that configuration 600 may fit on finger 602 in any orientation. In this manner, light source 502 may contact the finger 602 on any first side (e.g., left, bottom, etc.) of finger 602 while detector 504 may contact finger 602 on a second, opposite the first side of finger 602.

As light source 502 and detector 504 may be configured to be positioned on opposite sides of finger 602, configuration 600 may be configured to operate in a transmission mode, where photons are scattered by tissue within finger 602 and the photons that are transmitted through finger 602, via the scattering, are detected by detector 504. Detector 504 may be configured to detect arrival times of such photons at detector 504. As described, such arrival times may be used to determine histogram data, which may be used to determine one or more absolute optical properties.

Figure 7:
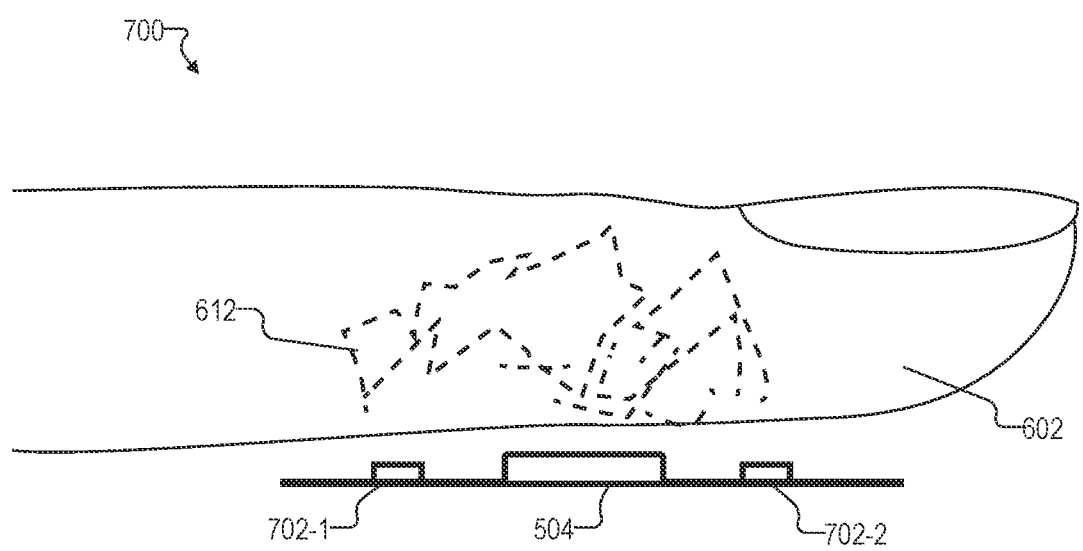

FIG. 7 illustrates another exemplary configuration 700 of optical measurement device 500. As shown, configuration 700 includes light sources 702-1 and 702-2 configured to emit light directed at finger 602. Configuration 700 further includes detector 504 configured to detect photons after the light has been scattered by finger 602. While not shown in FIG. 7, configuration 700 may further include processing unit 506 and a housing (e.g., housing 604) configured to house components of device 500.

Light sources 702 may be each implemented as a laser, such as any of the lasers described herein, and may be configured to direct light pulses at finger 602. In some examples, light source 702-1 may emit light at a first wavelength and light source 702-1 may emit light at a second, different wavelength. For instance light source 702-1 may emit light in a red portion of the spectrum (e.g., 690 nanometers (nm)), while light source 702-2 may emit light at an infrared portion of the spectrum (e.g., 850 nm), Alternatively, light source 702-1 and light source 702-2 may emit light at a same wavelength or wavelengths.

In this example, light sources 702 are positioned on a same side of the finger as detector 504. For instance, a housing (e.g., housing 604) may be configured to house light sources 702 and detector 504 in a first portion (e.g., portion 606-1) configured to contact a bottom (or any other side) of finger 602. Consequently, configuration 700 may be configured to operate in a reflectance mode, where photons are scattered by tissue within the finger and the photons that are reflected via the scattering are detected by detector 504. Detector 504 may determine arrival times of such photons and used as described herein.

Figure 8:
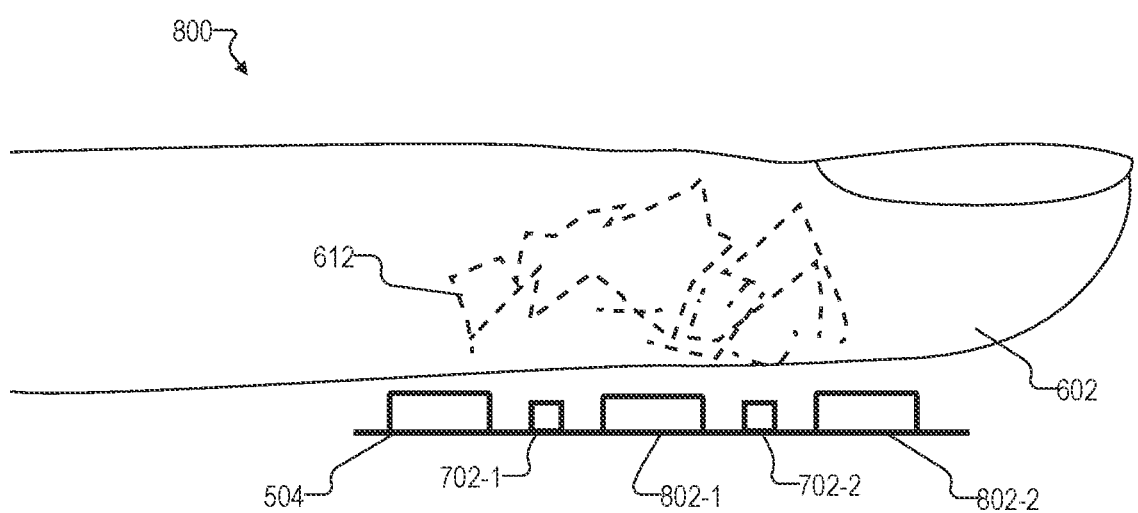
Figure 9:
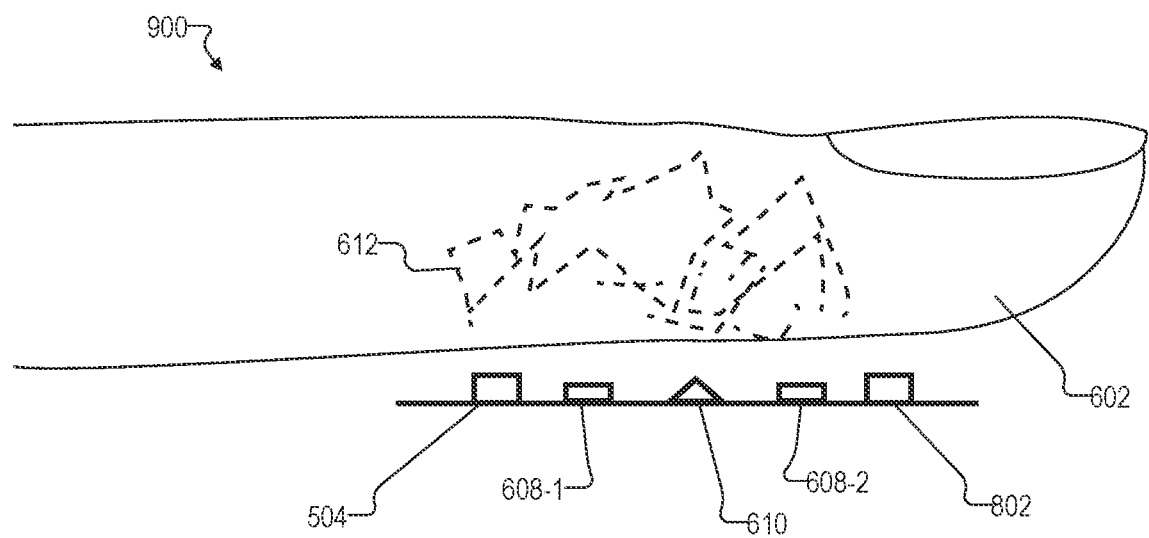

FIG. 8 illustrates another exemplary configuration 800 of optical measurement device 500. Configuration 800 is similar to configuration 700, including light sources 702 and detector 504 housed in a housing (e.g., housing 604, not shown). However, configuration 800 may further include two additional detectors 802 (e.g., detector 802-1 and detector 802-2). Like configuration 700, the additional detectors 802 may be configured to be positioned on a same side as light sources 702 and detector 504. Detectors 504 and 802 may be coupled to a global reference clock so that detectors 504 and 802 may measure data simultaneously, The outputs of detectors 504 and 802 may be combined to generate a single histogram from the photons detected by each of detectors 504 and 802. Alternatively, separate histograms may be generated that processing unit 506 may use for determining absolute optical properties, FIG. 9 illustrates another exemplary configuration 900 of optical measurement device 500, Configuration 900 is similar to configuration 600, including light source 502 implemented by lasers 608 and prism 610. However, configuration 900 further includes detector 504 and additional detector 802 housed in a housing (e.g., housing 604, not shown). Like configuration 800, detector 802 may be configured to be positioned on a same side as light source 502 and detector 504, and the outputs of detectors 504 and 802 may be combined to generate a single histogram from the photons detected by each of detectors 504 and 802. Alternatively, separate histograms may be generated that processing unit 506 may use for determining absolute optical properties.

While FIGS. 6-9 show a variety of geometries and form factors of optical measurement device 500, it will be recognized that only optical components of device 500 are shown in FIGS. 6-9 and that each device 500 may include any suitable housing and display screen and other internal or external components of device 500. Further, while FIGS. 6-9 show particular examples of numbers and positions of light sources and/or detectors, any suitable combination of light sources and detectors may be used to implement device 500.

Figure 10:
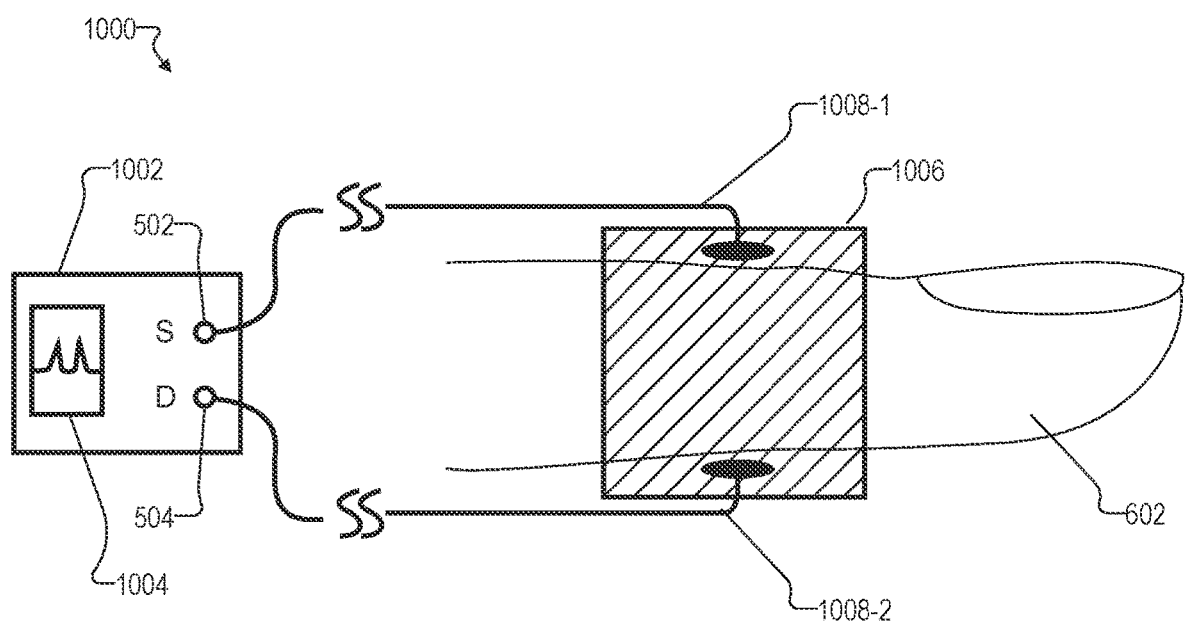

FIG. 10 illustrates another exemplary configuration 1000 of optical measurement device 500. Configuration 1000 includes a housing 1002 configured to house light source 502 and detector 504. In some embodiments, housing 1002 may further house processing unit 506 (not shown). Housing 1002 may further include a display 1004 configured to display outputs from processing unit 506, such as a blood oxygenation level or other characteristics of a user.

Configuration 1000 further includes a head-portion 1006 that is configured to fit on finger 602. Configuration 1000 includes optical conduits 1008 (e.g., optical conduit 1008-1, which may be an implementation of optical conduit 114 shown in FIG. 1, and optical conduit 1008-2, which may be an implementation of optical conduit 116 shown in FIG. 1) that connect housing 1002 and head-portion 1006. Optical conduit 1008-1 may connect light source 502 to head-portion 1006 and direct light pulses emitted from light source 502 to the finger. Optical conduit 1008-2 may connect detector 504 to head-portion 1006 and direct photons of the light pulses to detector 504 after the photons are scattered by tissue within finger 602. As shown, optical conduit 1008-1 may direct light pulses to one side of finger 602 while optical conduit 1008-2 may direct photons transmitted to an opposite side of finger 602. Additionally or alternatively, optical conduit 1008-2 may direct photons that are reflected back to a same side of finger 602 and/or transmitted to a different side of finger 602.

In some examples, head-portion 1006 may be configured to be disposable. Optical conduits 1008 or portions of optical conduits 1008 may also be configured to be disposable. The disposable portions of optical conduits 1008 may be configured to be coupled to another optical conduit connected to housing 1002 or directly coupled to housing 1002. Housing 1002, in contrast, may be configured to be non-disposable. Having a disposable head-portion 1006, while housing components in non-disposable housing 1002, may allow for a configuration of device 500 to be conveniently and cost-effectively used in a safe and sanitary manner.

Figure 11:
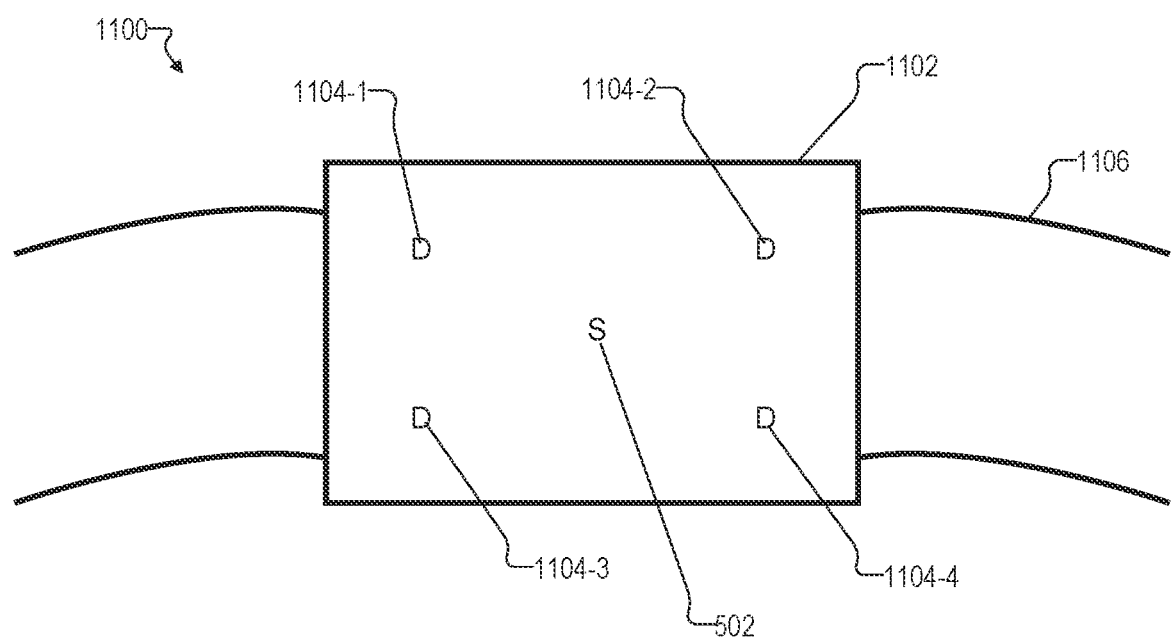
FIGS. 11-13 show optical measurement devices that may implement the optical measurement systems described herein and that may be in the form of a wrist-worn device.

FIG. 11 illustrates an exemplary configuration 1100 of an optical measurement device (e.g., device 500). Configuration 1100 includes a housing 1102 that is configured to house light source 502 and detectors 1104 (e.g., detectors 1104-1 through 1104-4, which may be implementations of detector 504). Housing 1102 may be further house processing unit 506 and/or any other components of device 500. Configuration 1100 may be configured to be worn on a wrist of a user (e.g., as part of a smart watch, a fitness tracker, etc.), and may include straps 1106 that may be configured to wrap around the wrist.

Figure 12:
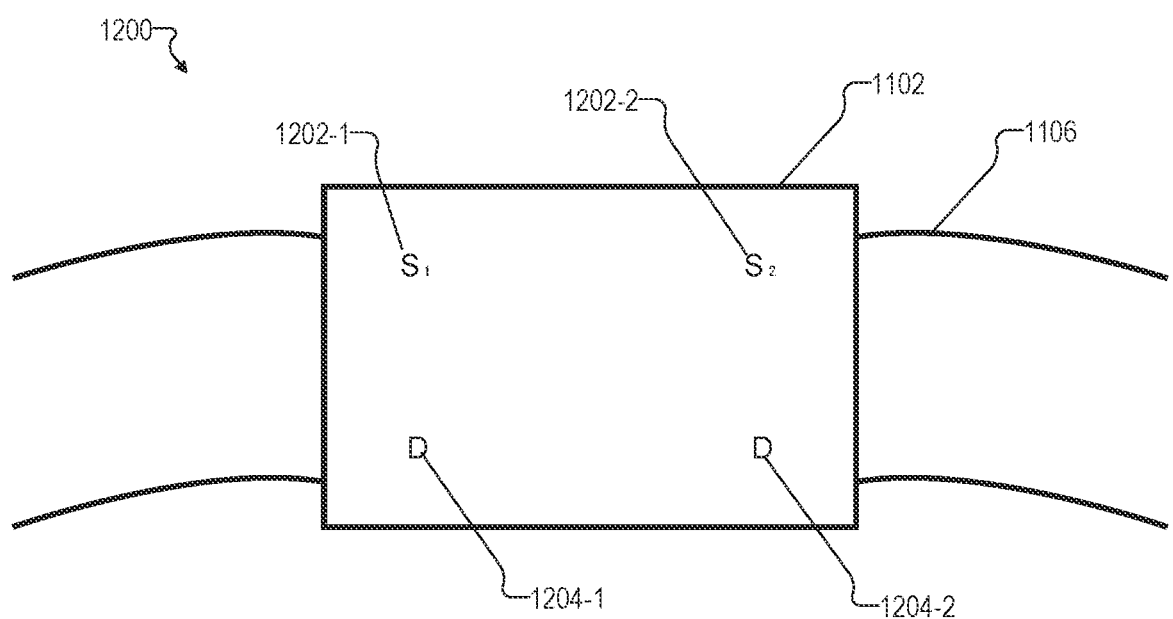

Light source 502 may be configured to emit light at two wavelengths (e.g., 690 nm and 850 nm, or any other suitable wavelengths) or any other suitable number of wavelengths. For instance, light source 502 may be implemented using two lasers emitting light at the respective wavelengths, coupled into a single location using a prism (e.g., lasers 608 and prism 610 shown in FIG. 6). Detectors 1104 may be configured to detect arrival times of photons that are scattered by tissue within the wrist of the user and reflected back to device 500. The detected arrival times may be used to generate histogram data as described herein, FIG. 12 illustrates another exemplary configuration 1200 of an optical measurement device (e.g., device 500). Configuration 1200 is similar to configuration 1100, including housing 1102 and straps 1106. However, in FIG. 12, housing 1102 may be configured to house light sources 1202 (e.g., light source 1202-1 and light source 1202-2) and detectors 1204 (e.g., detector 1204-1 and detector 1204-2).

Light sources 1202 may be similar to any of the light sources described herein. For instance, light source 1202-1 may emit light at a first wavelength and light source 1202-2 may emit light at a second wavelength. Light sources 1202 may be separated by a distance so that there may be a mix of source and detector distances. Further, diagonal paths of the two wavelengths may intersect in a middle of light sources 1202 and detectors 1204.

Detectors 1204 may be similar to any of the detectors described herein. Additionally or alternatively, detector 1204-1 may be configured to detect arrival times of photons to determine an absolute optical property associated with the wrist of the user, while detector 1204-2 may be configured to detect an absorption of light for determining a relative optical property associated with the wrist. For example, a processing unit (e.g., processing unit 506) may be configured to determine, based on output of detector 1204-1, an absorption coefficient and/or a reduced scattering coefficient of the wrist of the user. Processing unit 506 may be further configured to determine, based on output of detector 1204-2, a change in absorption of the wrist of the user. Processing unit 506 may further determine, based on the change in absorption, a blood oxygenation level of the user. Thus, processing unit 506 may operate based on detector 1204-2 similar to a continuous wave pulse oximeter. However, using measurements from detector 1204-1, processing unit 506 may also determine a blood oxygenation level of the user based on the absolute optical property. Processing unit 506 may then calibrate the blood oxygenation level determined using the relative optical property based on the blood oxygenation level determined using the absolute optical property.

By implementing the continuous wave pulse oximetry and determining the blood oxygenation level of the user based on the relative optical property, device 500 may conserve power as compared to determining the blood oxygenation level based on the absolute optical property using TD-NIRS. For example, device 500 may be configured to run generally using the continuous wave pulse oximetry while periodically calibrating the output using the blood oxygenation level determined based on the absolute optical property. In this manner, device 500 may use less power while also providing more accurate readings than a conventional continuous wave pulse oximeter.

Figure 13:
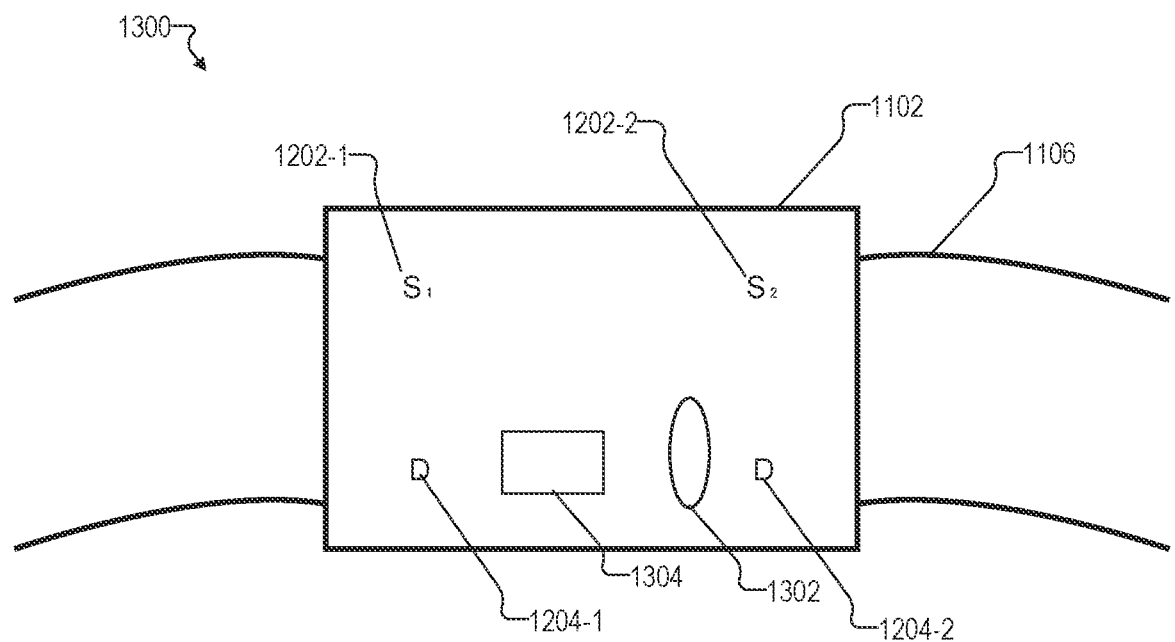

FIG. 13 illustrates another exemplary configuration 1300 of an optical measurement device (e.g., device 500). Configuration 1300 maybe similar to configuration 1200, including housing 1102, which houses light sources 1202 and detectors 1204, and straps 1106.

However, configuration 1300 may further include optical components 1302 and electronics components 1304 configured to disperse light rays representative of screen contents of device 500. Such dispersing of light rays may be configured to project and/or reflect the screen contents. For instance optical components 1302 and electronics components 1304 may include components of an image projection unit (e.g., one or more optical lenses, multi-colored LEDs, etc.) configured to project screen contents onto a ground surface in a vicinity of the user (e.g., on the ground in front of or to the side of where the user is walking, running, riding, etc.). Additionally or alternatively, the image projection unit may project the screen contents at an approximate eye level of a user, so that the user may raise a hand (e.g., a hand opposite the wrist on which device 500 is worn) at the eye level and see the screen contents projected on the hand. Additionally or alternatively, the image projection unit may project the screen contents on a hand or an arm adjacent to the wrist on which device 500 is worn. Additionally or alternatively, the image projection unit may project a three-dimensional image that presents the screen contents. Such projection of screen contents may allow the user to easily access information provided by device 500, for instance during outdoor activities such as running, hiking, etc.

Such projection or any other presentation of screen contents (e.g., a turning on of a display screen of device 500) may be based on the blood oxygenation level and/or characteristics determined by device 500 (e.g., a heart rate, a respiratory rate, a distance traveled, a number of steps, etc.). For example, such content may be displayed when the blood oxygenation level or the heart rate meets a predetermined threshold level.

Figure 14:
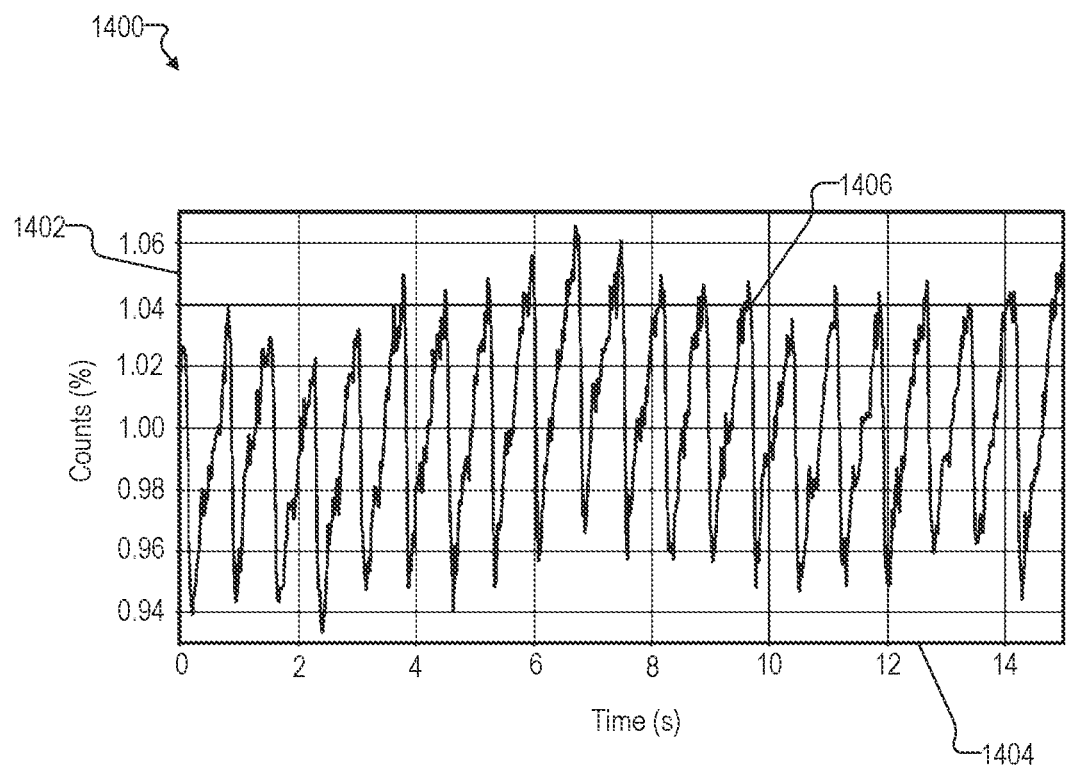
FIG. 14 shows an example graph showing heart rate as generated or recorded by any of the optical measurement devices described herein.

FIG. 14 shows an example graph 1400 showing heart rate as generated or recorded by an optical measurement device (e.g., device 500). Graph 1400 shows counts in percentage on a y-axis 1402 and time in seconds on an x-axis 1404. Line 1406 shows the heart rate, which may be determined using histogram data generated on arrival times of photons detected by device 500. Based on line 1406, heart rate variability (HRV) may also be determined by device 500. Such data may be used in any suitable manner, such as being provided as content to a user, for determining characteristics associated with the user, or any other manner as described herein.

Figure 15:
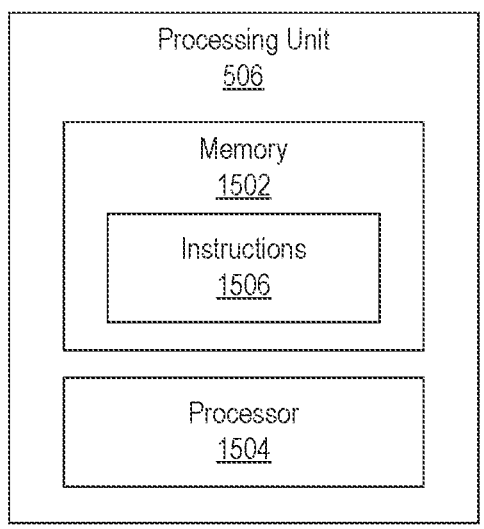
FIG. 15 illustrates an exemplary implementation of a processing unit.

FIG. 15 illustrates an exemplary implementation of processing unit 506 in which processing unit 506 includes a memory 1502 and a processor 1504 configured to be selectively and communicatively coupled to one another. In some examples, memory 1502 and processor 1504 may be distributed between multiple devices and/or multiple locations as may serve a particular implementation.

Memory 1502 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1502 may maintain (e.g., store) executable data used by processor 1504 to perform one or more of the operations described herein. For example, memory 1502 may store instructions 1506 that may be executed by processor 1504 to perform any of the operations described herein. Instructions 1506 may be implemented by any suitable application, program (e.g., sound processing program), software, code, and/or other executable data instance. Memory 1502 may also maintain any data received, generated, managed, used, and/or transmitted by processor 1504.

Processor 1504 may be configured to perform (e.g., execute instructions 1506 stored in memory 1502 to perform) various operations described herein. For example, processor 1504 may be configured to perform any of the operations described herein as being performed by processing unit 506.

In some examples, processing unit 506 may be included in the same wearable device that includes light source 502 and detectors 504. Alternatively, processing unit 506 is not included in the same wearable device that includes light source 502 and detector 504. For example, processing unit 506 may be implemented by a stand-alone computing device (e.g., a smart phone, laptop, etc.) communicatively coupled to the wearable device by way of one or more communication interfaces (e.g., cables, wireless interfaces, etc.).

Figure 16:
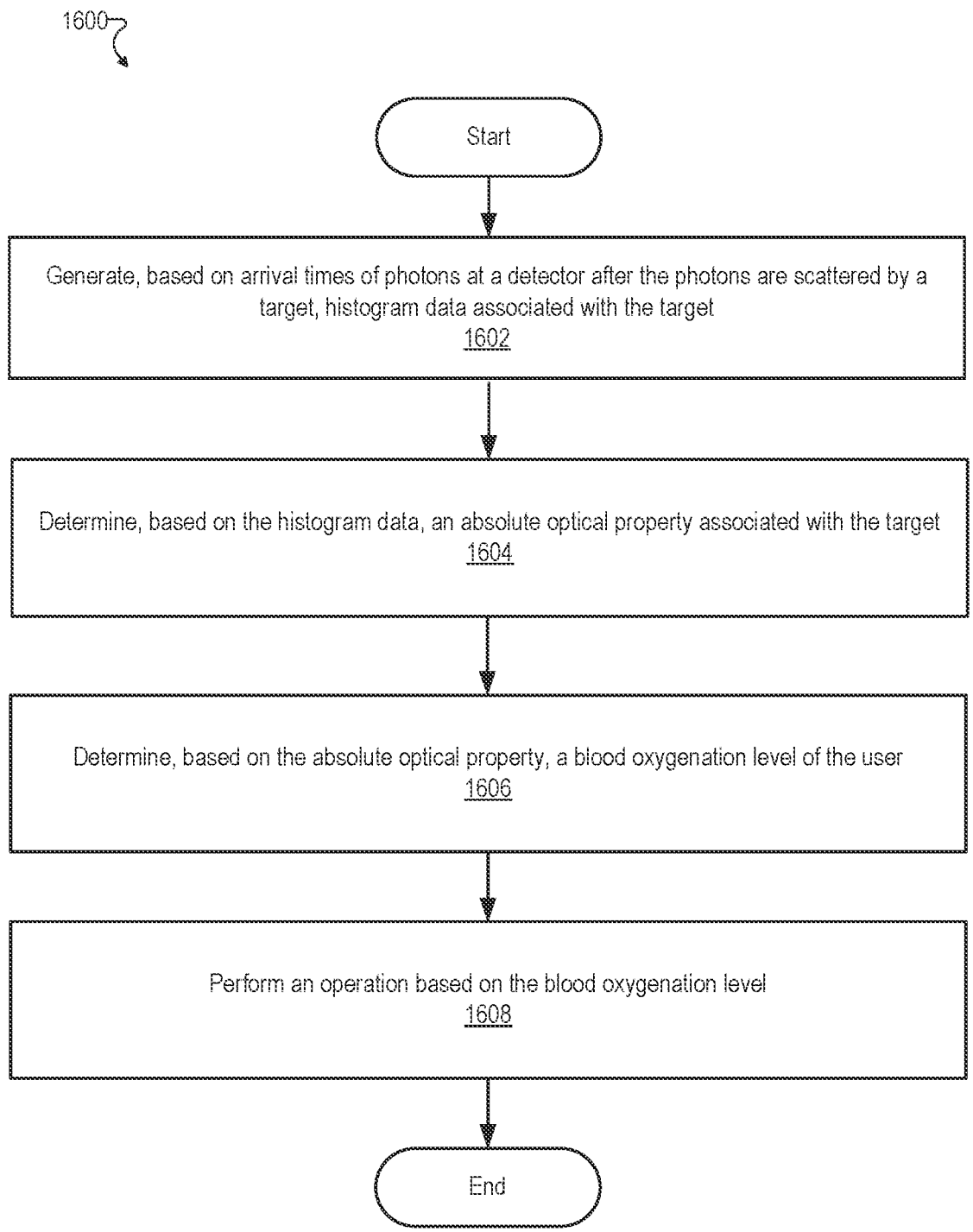
FIG. 16 illustrate an exemplary method.

FIG. 16 illustrates an exemplary method 1600 that may be performed by processing unit 506 and/or any implementation thereof. While FIG. 16 illustrates exemplary operations according to one embodiment, other embodiments may omit, add to, reorder, and/or modify any of the operations shown in FIG. 16. Each of the operations shown in FIG. 16 may be performed in any of the ways described herein.

At operation 1602, a processing unit generates, based on arrival times of photons at a detector after the photons are scattered by a target, histogram data associated with the target.

At operation 1604, the processing unit determines, based on the histogram data, an absolute optical property associated with the target.

At operation 1606, the processing unit determines, based on the absolute optical property, a blood oxygenation level of the user.

At operation 1608, the processing unit performs an operation based on the blood oxygenation level. For example, one type of operation may include processing the blood oxygenation level and/or histogram data in order to determine respiratory rate; another type of operation may include processing the blood oxygenation level and/or histogram data in order to determine heart rate; and yet another type of operation may include processing the blood oxygenation level and/or histogram data in order to determine heart rate variability.

An illustrative optical measurement device includes a light source configured to emit light pulses directed at a target. The optical measurement device further includes a detector configured to detect arrival times for photons of the light pulses after the photons are scattered by the target. The optical measurement device further includes a processing unit configured to generate, based on the arrival times of the photons at the detector, histogram data associated with the target. The processing unit is further configured to determine, based on the histogram data, an absolute optical property associated with the target. The processing unit is further configured to determine, based on the absolute optical property, a blood oxygenation level of the user, and perform an operation based on the blood oxygenation level.

Another illustrative optical measurement device includes a light source configured to emit light pulses directed at an appendage of a user. The optical measurement device further includes a detector configured to detect arrival times for photons of the light pulses after the photons are scattered by tissue within the appendage. The optical measurement device further includes a housing configured to house the light source and the detector. The optical measurement device further includes a processing unit configured to generate, based on the arrival times of the photons at the detector, histogram data associated with the appendage. The processing unit is further configured to determine, based on the histogram data, an absolute optical property associated with the appendage. The processing unit is further configured to determine, based on the absolute optical property, a blood oxygenation level of the user.

Another illustrative optical measurement device includes a light source configured to emit light directed at a wrist of a user. The optical measurement device further includes a detector configured to detect arrival times for photons of the light after the photons are scattered by tissue within the wrist. The optical measurement device further includes a housing configured to house the light source, the detector, and a processing unit. The optical measurement device further includes a strap coupled to the housing and configured to hold the housing against the wrist. The optical measurement device further includes the processing unit configured to generate, based on the arrival times of the photons at the detector, histogram data associated with the wrist. The processing unit is further configured to determine, based on the histogram data, an absolute optical property associated with the wrist. The processing unit is further configured to determine, based on the absolute optical property, a blood oxygenation level of the user.

Another illustrative optical measurement device includes a light source configured to emit light directed at a wrist of a user. The optical measurement device further includes a detector configured to detect arrival times for photons of the light after the photons are scattered by tissue within the wrist. The optical measurement device further includes an image projection unit. The optical measurement device further includes a processing unit configured to generate, based on the arrival times of the photons at the detector, histogram data associated with the wrist. The processing unit is further configured to determine, based on the histogram data, an absolute optical property associated with the wrist. The processing unit is further configured to determine, based on the absolute optical property, a blood oxygenation level of the user. The processing unit is further configured to determine, based on the blood oxygenation level of the user, information associated with the user. The processing unit is further configured to direct the image projection unit to project the information.

Another illustrative optical measurement device includes a light source configured to emit light directed at a target. The optical measurement device further includes a first detector configured to detect arrival times for photons of the light after the photons are scattered by the target. The optical measurement device further includes a second detector configured to detect an absorption of the light by the target. The optical measurement device further includes a processing unit configured to generate, based on the arrival times of the photons at the detector, histogram data associated with the target. The processing unit is further configured to determine, based on the histogram data, an absolute optical property associated with the target. The processing unit is further configured to determine, based on the absolute optical property, a first blood oxygenation level of the user. The processing unit is further configured to determine, based on the absorption of the light by the target, a relative optical property associated with the target. The processing unit is further configured to determine, based on the relative optical property, a second blood oxygenation level of the user. The processing unit is further configured to calibrate the second blood oxygenation level based on the first blood oxygenation level.

An illustrative method includes generating, by a processing unit, based on arrival times of photons at a detector after the photons are scattered by a target of a user, histogram data associated with the target. The method further includes determining, by the processing unit, based on the histogram data, an absolute optical property associated with the target. The method further includes determining, by the processing unit, based on the absolute optical property, a blood oxygenation level of the user. The method further includes performing, by the processing unit, an operation based on the blood oxygenation level.

An illustrative non-transitory computer-readable medium stores instructions that, when executed, direct a processor of a computing device to generate, based on arrival times of photons at a detector after the photons are scattered by a target of a user, histogram data associated with the target. The instructions further direct the processor to determine, based on the histogram data, an absolute optical property associated with the target. The instructions further direct the processor to determine, based on the absolute optical property, a blood oxygenation level of the user. The instructions further direct the processor to perform, an operation based on the blood oxygenation level.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A wearable optical measurement device for use by a user, the wearable optical measurement device comprising:
   a light source configured to emit light pulses directed at a target;
   a detector configured to detect arrival times for photons of the light pulses after the photons are scattered by the target; and
   a processing unit configured to:
      generate, based on the arrival times of the photons at the detector, histogram data associated with the target;
      determine, based on the histogram data, an absolute optical property associated with the target;
      determine, based on the absolute optical property, a blood oxygenation level of the user;
      perform an operation based on the blood oxygenation level;
      determine, based on the histogram data, at least one of a heart rate, a heart rate variability, or a respiratory rate of the user; and
      access inertial measurement unit (IMU) data associated with the user;
      wherein the performing the operation comprises determining a sleep stage of the user based on the blood oxygenation level, the IMU data, and the at least one of the heart rate, the heart rate variability, or the respiratory rate.

2. The wearable optical measurement device of claim 1, wherein the performing the operation comprises outputting data representative of the blood oxygenation level.

3. The wearable optical measurement device of claim 1, wherein the performing the operation comprises providing content associated with the blood oxygenation level for presentation to the user.

4. The wearable optical measurement device of claim 3, wherein the content comprises a recommendation based on the blood oxygenation level.

5. The wearable optical measurement device of claim 3, wherein the providing the content for presentation comprises displaying, on a screen of the wearable optical measurement device, the blood oxygenation level.

6. The wearable optical measurement device of claim 3, wherein the providing the content for presentation comprises providing an alert based on the blood oxygenation level meeting a predetermined threshold blood oxygenation level.

7. The wearable optical measurement device of claim 3, wherein the providing the content for presentation comprises directing an image projection unit of the wearable optical measurement device to project the content.

8. The wearable optical measurement device of claim 7, wherein the directing the image projection unit to project the content comprises directing the image projection unit to project the content on a ground surface in a vicinity of the user.

9. The wearable optical measurement device of claim 7, wherein the directing the image projection unit to project the content comprises directing the image projection unit to project the content at an approximate eye level of the user.

10. The wearable optical measurement device of claim 7, wherein the directing the image projection unit to project the content comprises directing the image projection unit to project the content on a hand or arm of the user.

11. The wearable optical measurement device of claim 1, further comprising a housing configured to fit on an appendage of the user and house the light source and the detector.

12. The wearable optical measurement device of claim 11, wherein the housing is further configured to house the processing unit.

13. The wearable optical measurement device of claim 1, further comprising a housing configured to be worn on a wrist of the user and house the light source and the detector.

14. The wearable optical measurement device of claim 13, wherein the housing is further configured to house the processing unit.

15. A wearable optical measurement device configured to be worn on an appendage of a user, the wearable optical measurement device comprising:
- a light source configured to emit light pulses directed at the appendage;
- a detector configured to detect arrival times for photons of the light pulses after the photons are scattered by tissue within the appendage;
- a housing configured to house the light source and the detector; and
- a processing unit configured to:
  - generate, based on the arrival times of the photons at the detector, histogram data associated with the appendage;
  - determine, based on the histogram data, an absolute optical property associated with the appendage;
  - determine, based on the absolute optical property, a blood oxygenation level of the user;
  - determine, based on the histogram data, at least one of a respiratory rate of the user, a heart rate of the user, or a heart rate variability of the user;
  - access inertial measurement unit (IMU) data associated with the user; and
  - determine, based on the IMU data, and the at least one of the heart rate, the heart rate variability, or the respiratory rate, a sleep stage of the user.

16. The wearable optical measurement device of claim 15, wherein the housing is further configured to house the processing unit.

17. The wearable optical measurement device of claim 15, wherein:
- the light source comprises two lasers and a prism;
- the lasers are configured to direct light pulses at the prism; and
- the prism is configured to direct the light pulses at the appendage.

18. The wearable optical measurement device of claim 15, wherein the light source comprises a vertical-cavity surface-emitting laser (VCSEL).

19. The wearable optical measurement device of claim 15, wherein the housing is configured to fit on the appendage and comprises:
- a first portion configured to house the light source and contact a first side of the appendage; and
- a second portion configured to house the detector and contact a second side of the appendage, the second side opposite the first side.

20. The wearable optical measurement device of claim 15, wherein the housing is configured to fit on the appendage and the light source and the detector are configured to be positioned on a same side of the appendage of the user.

21. The wearable optical measurement device of claim 15, further comprising:
- a disposable head-portion configured to fit on the appendage;
- a first optical conduit from the light source to the disposable head-portion, the first optical conduit configured to direct the light pulses at the appendage; and
- a second optical conduit from the disposable head-portion to the detector, the second optical conduit configured to direct the photons scattered by the tissue within the appendage to the detector.

22. The wearable optical measurement device of claim 15, wherein the processing unit is further configured to perform an operation based on the blood oxygenation level.

23. The wearable optical measurement device of claim 22, wherein the performing the operation comprises providing content associated with the blood oxygenation level for presentation to the user.

24. A wearable optical measurement device configured to be worn on a wrist of a user, the wearable optical measurement device comprising:
- a light source configured to emit light directed at the wrist;
- a detector configured to detect arrival times for photons of the light after the photons are scattered by tissue within the wrist;
- a housing configured to house the light source, the detector, and a processing unit;
- a strap coupled to the housing and configured to hold the housing against the wrist; and
- the processing unit configured to:
  - generate, based on the arrival times of the photons at the detector, histogram data associated with the wrist;
  - determine, based on the histogram data, an absolute optical property associated with the wrist;
  - determine, based on the absolute optical property, a blood oxygenation level of the user;
  - determine, based on the histogram data, at least one of a respiratory rate of the user, a heart rate of the user, or a heart rate variability of the user;
  - access inertial measurement unit (IMU) data associated with the user; and
  - determine, based on the IMU data, and the at least one of the heart rate, the heart rate variability, or the respiratory rate, a sleep stage of the user.

* * * * *